(12) United States Patent
Ginn

(10) Patent No.: US 7,128,747 B2
(45) Date of Patent: Oct. 31, 2006

(54) APPARATUS AND METHODS FOR REDUCING LUNG VOLUME

(75) Inventor: Richard S. Ginn, San Jose, CA (US)

(73) Assignee: Gateway Medical, Sunnyvale, CA (US)

( * ) Notice: Subject to any disclaimer, the term of this patent is extended or adjusted under 35 U.S.C. 154(b) by 261 days.

(21) Appl. No.: 10/682,458

(22) Filed: Oct. 8, 2003

(65) Prior Publication Data

US 2004/0073207 A1    Apr. 15, 2004

Related U.S. Application Data

(63) Continuation of application No. 09/931,681, filed on Aug. 15, 2001, now Pat. No. 6,645,205.

(51) Int. Cl.
*A61B 17/24* (2006.01)
(52) U.S. Cl. ................. 606/108; 606/213; 128/200.14; 623/9
(58) Field of Classification Search ................. 606/108, 606/213; 128/200.14, 200.24; 623/9
See application file for complete search history.

(56) References Cited

U.S. PATENT DOCUMENTS

| | | |
|---|---|---|
| 3,683,655 A | 8/1972 | White et al. |
| 3,757,783 A | 9/1973 | Alley |
| 5,306,234 A | 4/1994 | Johnson |
| 5,588,424 A | 12/1996 | Insler et al. |
| 5,588,992 A | 12/1996 | Scott et al. |
| 5,707,352 A | 1/1998 | Sekins et al. |
| 5,855,601 A | 1/1999 | Bessler et al. |
| 5,904,648 A | 5/1999 | Arndt et al. |
| 5,954,636 A | 9/1999 | Schwartz et al. |
| 5,954,766 A | 9/1999 | Zadno-Azizi et al. |
| 6,003,517 A | 12/1999 | Sheffield et al. |
| 6,020,380 A | 2/2000 | Killian |
| 6,027,525 A | 2/2000 | Suh et al. |
| 6,174,323 B1 | 1/2001 | Biggs et al. |
| 6,258,100 B1 | 7/2001 | Alferness et al. |
| 6,287,290 B1 | 9/2001 | Perkins et al. |

(Continued)

FOREIGN PATENT DOCUMENTS

WO    WO 01/66190    3/2001

(Continued)

OTHER PUBLICATIONS

Clifton A. Alferness, et al., EPO Publication No. EP 1 078 601 A2, "Lung Volume Reduction Apparatus", Feb. 28, 2001.

(Continued)

*Primary Examiner*—Lee S. Cohen
(74) *Attorney, Agent, or Firm*—Orrick, Herrington & Sutcliffe LLP

(57) ABSTRACT

Apparatus and methods are provided for reducing the volume of a lung using a clip including a plurality of tines. The clip is advanced along an interior of a bronchial passage to a predetermined location with the tines in a contracted condition. The tines are expanded outwardly to engage surrounding tissue, and then collapsed towards the contracted condition, thereby drawing the surrounding tissue inwardly to substantially close the bronchial passage from air flow therethrough. Optionally, electrical energy may be applied to the surrounding tissue after collapsing the tines to the contracted condition, thereby fusing the surrounding tissue together. The clip is then released within or removed from the passage.

7 Claims, 10 Drawing Sheets

U.S. PATENT DOCUMENTS

| | | |
|---|---|---|
| 6,293,951 B1 | 9/2001 | Alferness et al. |
| 6,327,505 B1 | 12/2001 | Medhkour et al. |
| 6,348,064 B1 | 2/2002 | Kanner |
| 6,599,311 B1 * | 7/2003 | Biggs et al. ............... 606/232 |
| 2001/0037808 A1 | 11/2001 | Deem et al. |
| 2001/0052344 A1 | 12/2001 | Doshi |
| 2002/0112729 A1 | 8/2002 | DeVore et al. |

FOREIGN PATENT DOCUMENTS

| WO | WO 01/87170 | 5/2001 |
|---|---|---|

OTHER PUBLICATIONS

T. Sabanathan, PCT Publication No. WO 98/48706, "Occlusion Device", Nov. 5, 1998.

C. Danek, et al., PCT Publication No. WO 00/62699, "Modification of Airways by Application of Energy", Oct. 26, 2000.

Rodney A. Perkins, et al., PCT Publication No. WO 01/02042 A1, "Methods, Systems, and Kits for Lung Volume Reduction", Jan. 11, 2001.

Clifton A. Alferness, et al., PCT Publication No. WO 01/13839 Amendment, Lung Reduction Device, System, and Method, Mar. 1, 2001.

Edward P. Ingenito, PCT Publication No. WO 01/13908 A2, "Tissue Volume Reduction", Mar. 1, 2001.

* cited by examiner

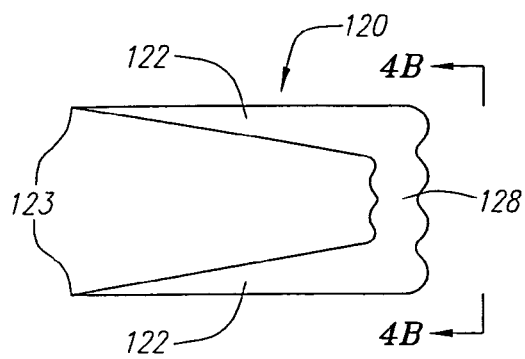
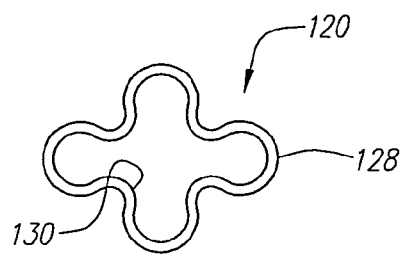
FIG. 4A  FIG. 4B
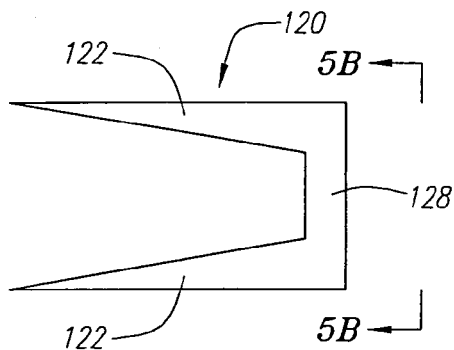
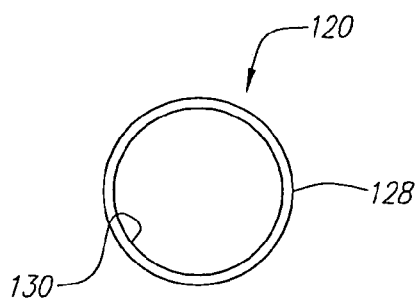
FIG. 5A  FIG. 5B
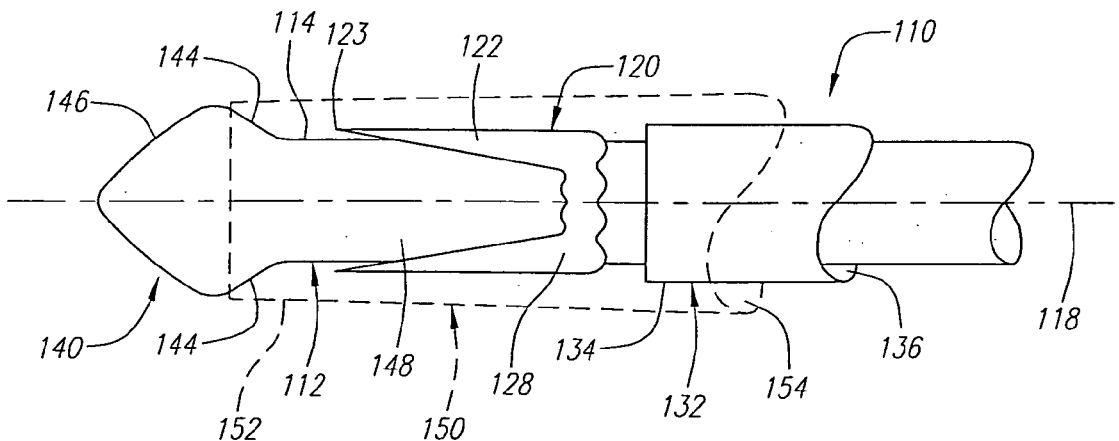
FIG. 6

APPARATUS AND METHODS FOR REDUCING LUNG VOLUME

RELATED INFORMATION

This application is a continuation of application Ser. No. 09/931,681 filed on Aug. 15, 2001, now U.S. Pat. No. 6,645,205. The priority of the prior application is expressly claimed, and the disclosure of this application is hereby incorporated by reference in its entirety.

FIELD OF THE INVENTION

The present invention relates generally to apparatus and methods for reducing the volume of a lung, and more particularly to apparatus and methods for isolating one or more regions of a lung using a clip that is deployed within a bronchus or other passage to reduce the effective volume of the lung.

BACKGROUND

Patients with chronic bronchitis or other chronic occlusive pulmonary disease ("COPD") may have reduced lung capacity and/or efficiency due to lung tissue breaking down. For example, in severe chronic pulmonary disease, e.g., emphysema, lung tissue may be damaged or destroyed, reducing the ability of the lung to effectively transfer oxygen. One of the problems with emphysema and like conditions is that the lungs become over-inflated, filling the chest cavity and preventing the patient from being able to inhale effectively.

In severe emphysema cases, lung volume reduction surgery ("LVRS") has been suggested to improve lung efficiency. LVRS is performed by opening the chest cavity, retracting the ribs, and stapling off and removing a diseased or partially diseased portion of a lung. This may allow the remaining healthier lung tissue to inflate more fully within the chest cavity, thereby increasing lung efficiency. LVRS, however, is an extremely invasive procedure, and exposes the patient to substantial post-operative complications.

Accordingly, apparatus and methods for reducing the volume of a lung while avoiding the need for open surgery would be considered useful.

SUMMARY OF THE INVENTION

The present invention is directed to apparatus and methods for reducing the volume of a lung, and more particularly to closure devices, and to apparatus and methods for delivering closure devices, such as a clip, within a bronchus or other bronchial passage to reduce the volume of a lung and/or to isolate one or more regions of a lung.

In accordance with a first aspect of the present invention, a clip or other closure device is provided for closing a bronchial passage that includes a generally annular body or collar from which a plurality of tines extend. The annular body defines an opening therethrough, which may be generally circular and/or may have a predetermined asymmetrical shape that allows the clip to be detachably coupled to a delivery apparatus, such as that described below. The tines are movable between a contracted condition, and preferably are biased towards the contracted condition, but are deflectable towards the expanded condition.

In a first embodiment, the tines may extend generally parallel to one another along an axis extending through the opening in the annular body in the contracted condition. Alternatively, the tines may be biased to extend towards one another such that the annular body and the tines generally define a plane. The tines may be deflected axially, i.e., generally parallel to one another, to provide a delivery configuration, and further deflected radially outward to define the expanded condition.

In another embodiment, the collar may be collapsible towards a contracted condition and expandable towards an expanded condition. Preferably, the collar is biased to collapse towards the contracted condition and may be expanded towards the expanded condition, e.g., to deploy the closure device and/or to enhance engagement with surrounding tissue.

In yet another embodiment, the closure device may include a plurality of elongate elements connected by an intermediate hinged region. The elongate elements may include first ends defining tissue penetrating tips, and second ends opposite the hinged region. The first ends may be biased towards one another, but may be deflected radially outwardly by compressing the second ends.

In accordance with a second aspect of the present invention, an apparatus is provided for isolating a region of a lung that includes an elongate member, including a proximal end and a distal end having a size for insertion into a body lumen, such as a bronchial passage. A closure device, such as one of the clips described above, may be carried by the distal end, the closure device including a plurality of tines that are movable between a contracted condition and an expanded condition. A deflecting element, such as a ramped surface, an anvil, and the like, is also carried by the distal end of the elongate member. At least one of the deflecting element and the closure device is movable relative to the other for deflecting the tines outwardly towards the expanded condition for engaging tissue surrounding the distal end. The tines are collapsible towards the contracted condition, e.g., using their inherent bias or using a hammer also carried by the elongate member, for drawing the surrounding tissue inwards to substantially close and/or seal the body lumen, as described further below.

If desired, one or more other devices may be associated with the apparatus. For example, the apparatus may also include a source of energy, e.g., a radio frequency (RF) electrical generator, associated with the elongate member. At least a portion of the closure device may be coupled to the source of energy for delivering energy to surrounding tissue engaged by the tines. For example, first and second tines may be electrically coupled to first and second leads, respectively, that extend through the elongate member. The first and second leads may be coupled to opposite terminals of the RF generator, thereby providing a bipolar arrangement for applying energy to tissue. Alternatively, a single lead may be coupled to the closure device, and an external electrode may be attached to an exterior surface of a patient for providing a monopolar arrangement. In a further alternative, a first lead may be coupled to the closure device, and a second lead may be coupled to a location on the distal end of the apparatus.

Alternatively or in addition, a bronchoscope or other imaging device may be associated with the apparatus for viewing beyond the distal end of the elongate member. For example, the elongate member may be a bronchoscope, a bronchoscope may be slidably inserted through a lumen in the elongate member, or a separate bronchoscope may be independently used along with the apparatus.

A separate insufflation or aspiration catheter may also be provided or the elongate member may include a separate lumen extending between the proximal and distal ends. A source of fluid, e.g., oxygen or helium, or other substance, e.g., a corrosive and/or bonding agent, may be connected to the elongate member for delivering the substance to a location beyond the distal end of the elongate member via the lumen. Alternatively, a source of vacuum may be connected to the elongate member for evacuating fluid, e.g., air, via the lumen.

In accordance with another aspect of the present invention, a method is provided for reducing the volume of a lung using a closure device including a plurality of tines movable between contracted and expanded conditions, such as those described above. The closure device may be advanced within a bronchial passage to a predetermined location with the tines in the contracted condition. At the predetermined location, preferably a branch communicating with a region of the lung intended to be isolated and/or collapsed, the tines may be expanded outwardly towards the expanded condition to engage tissue surrounding the predetermined location, e.g., the wall of the bronchial passage. The tines may then be collapsed towards the contracted condition, thereby drawing the surrounding tissue inwardly to substantially close and/or seal the bronchial passage from air flow through the predetermined location into and/or out of the region to be isolated.

If desired, energy, such as electricity or heat, and/or an adhesive may be applied to the surrounding tissue after collapsing the tines to the contracted condition, thereby at least partially fusing or bonding the surrounding tissue together. Alternatively or in addition, a corrosive and/or bonding agent may be introduced into the region to be isolated before delivering the closure device for scarring and/or fusing tissue in the region to be isolated. In a further alternative, a conductive fluid, e.g., saline, may be introduced into the region to be isolated before closing the bronchial passage, electrical energy delivered via the fluid to damage or scar the tissue, and the fluid may then be removed.

The closure device may then be released from the distal end after the tines have been collapsed to close the bronchial passage. Alternatively, the closure device may be withdrawn from the predetermined location after applying energy and/or an adhesive, which may be sufficient to close the bronchial passage without the closure device.

Other objects and features of the present invention will become apparent from consideration of the following description taken in conjunction with the accompanying drawings.

BRIEF DESCRIPTION OF THE DRAWINGS

FIGS. 4A and 4B are side and rear views, respectively, of a closure device for isolating a region of a lung in a contracted condition, in accordance with the present invention.

FIGS. 5A and 5B are side and rear views, respectively, of the closure device of FIGS. 4A and 4B in an expanded condition.

FIG. 6 is a side view of an apparatus for delivering the closure device of FIGS. 4A and 4B.

DETAILED DESCRIPTION OF THE PREFERRED EMBODIMENTS

Figure 1A:
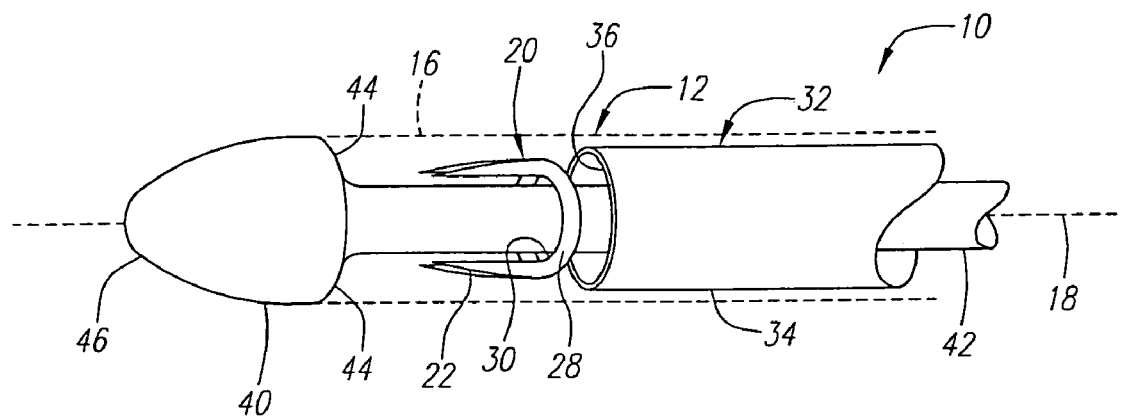
FIGS. 1A and 1B are perspective views of an apparatus for reducing volume of a lung, including a clip in contracted and expanded conditions, respectively, in accordance with the present invention.

Turning now to the drawings, FIGS. 1A–2B show a first preferred embodiment of an apparatus 10 for reducing volume of a lung, in accordance with the present invention. Generally, the apparatus 10 includes a sheath 12, a closure device or clip 20, a stop member 32, and a deflecting element 40.

The sheath 12 is an elongate tubular member including a proximal end (not shown), a distal end 16 having a size for insertion into a bronchial passage or other body lumen (not shown), and a longitudinal axis 18 extending between the proximal end and the distal end 16. The sheath 12 includes a lumen 24 extending between the proximal end and the distal end 16, and optionally may include one or more additional lumens (not shown), as described further below. The sheath 12 may be formed from a variety of known biocompatible materials, and may have a diameter between about two and twenty millimeters (2–20 mm), and a length between about twenty and two hundred centimeters (20–200 cm).

In one embodiment, the sheath 12 may be a bronchoscope, including a camera, lens, and/or light source (not shown) on the distal end 16 of the sheath 12. The lumen 24 may be a conventional instrument lumen provided in the bronchoscope or a special lumen configured for receiving the clip 20, stop member 32, and/or deflecting element 40. Alternatively, a bronchoscope, endoscope, or other imaging or visualization device (not shown) may be generally associated with the apparatus 10. For example, a separate bronchoscope or other device (not shown) may be provided that maybe independently introduced along with the apparatus 10 into a bronchial passage. Alternatively, the sheath 12 may include an additional lumen (not shown) through which a bronchoscope or other device may be advanced. In a further alternative, a camera, lens, and/or light source (not shown) may be provided on the deflecting element 40, as described further below.

The clip 20 is generally carried by the distal end 16 of the sheath 12 during delivery, for example, within a distal portion 26 of the lumen 24 such that the sheath 12 overlies the tines 22. Alternatively, the clip 20 may be carried on an exterior surface of the sheath 12 (not shown). The clip 20 is preferably detachably coupled to the sheath 12, the stop member 32, and/or the deflecting element 40, allowing the clip 20 to be delivered to and released at a predetermined location within a bronchial passage, as described further below.

The clip 20 generally includes an annular body or collar 28 from which a plurality of tines 22 extend. The collar 28 defines an opening 30 therethrough, which may be generally circular and/or may have a predetermined shape that allows the clip 20 to be detachably coupled to the apparatus 10, such as the deflecting element 40, as described further below. The tines 22 are movable between a contracted condition (shown in FIGS. 1A, 2A) and an expanded condition (shown in FIGS. 1B, 2B). Although the exemplary embodiment of the clip 20 shown includes four tines 22, any number of tines may be provided, as will be appreciated by those skilled in the art.

Preferably, the tines 22 are biased towards the contracted condition, but are deflectable towards the expanded condition. The clip 20 may be formed from a single sheet of biocompatible material, e.g., a metal, such as stainless steel or Nitinol, or plastic. Preferably, the clip 20 is formed from an elastic or superelastic material, e.g., Nitinol, such that the tines 22 may be biased to compress towards the contracted condition, but may be resiliently expanded to the expanded condition. Alternatively, the tines 22 may be plastically deformable towards the contracted and/or expanded conditions.

Figure 1B:
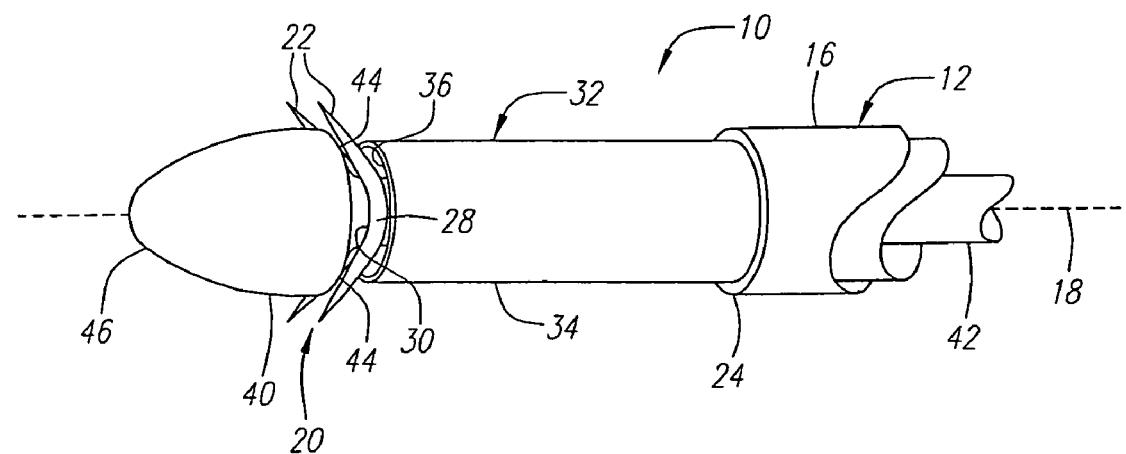
Figure 2A:
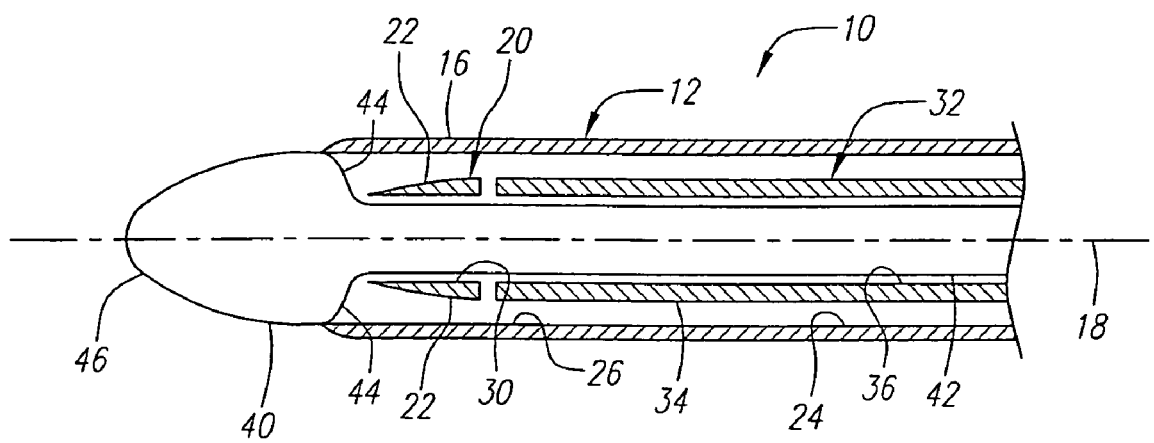
FIGS. 2A and 2B are cross-sectional side views of the apparatus of FIGS. 1A and 1B, respectively.
Figure 2B:
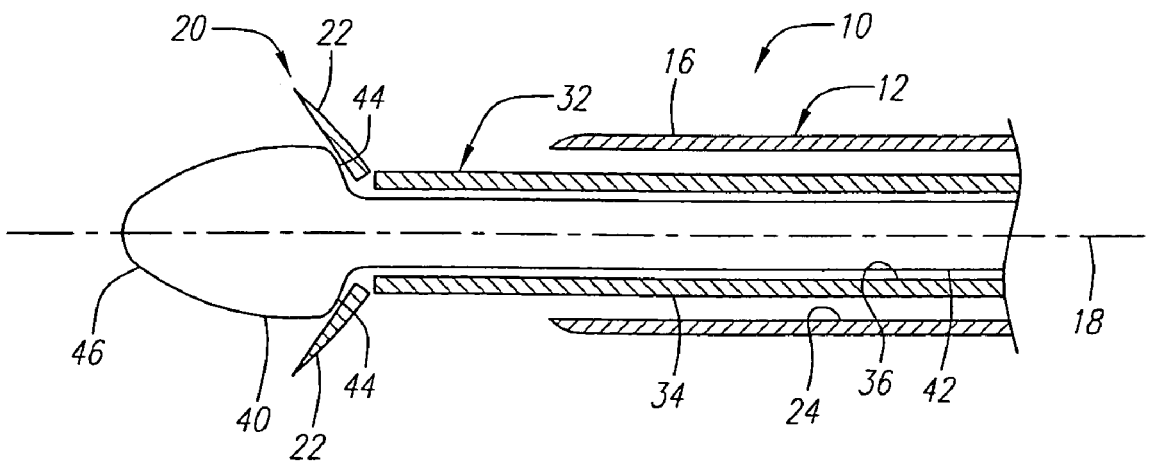

In the contracted condition, the tines 22 may extend generally parallel to the longitudinal axis 18 of the sheath 12 in the contracted condition, as shown in FIGS. 1A and 1B. Alternatively, the tines 22 may be biased to extend towards one another such that the collar 28 and tines 22 generally define a plane. Thus, the tines 22 may be deflected axially, as shown in FIGS. 1A and 2A, to provide a delivery configuration, and further deflected radially outward to define an expanded condition, as shown in FIGS. 1B and 2B. Exemplary clips of this configuration that may be incorporated into an apparatus in accordance with the present invention are disclosed in application Ser. No. 09/732,178, filed Dec. 7, 2000, the disclosure of which is expressly incorporated herein by reference.

The stop member 32 is also disposed within the lumen 24 of the sheath 12 proximal to the clip 20. The stop member 32 includes a proximal end (not shown), a distal end 34, and a lumen 36 extending therebetween. The stop member 32 is also preferably tubular, similar to the sheath 12, and may be formed to slidably fit in close proximity to an inner wall of the sheath 12. Preferably, the distal end 34 is substantially blunt or otherwise formed to restrain the clip 20 from axial movement, e.g., during retraction of the sheath 12, or to advance the clip 20 from the sheath 12, as described further below.

The deflecting element 40 is also carried by the distal end 16 of the sheath 12 or otherwise associated with the clip 20. Preferably, the deflecting element 40 is connected to a cable, wire, or other control member 42 that extends proximally through the lumen 36 of the stop member 32. Thus, the deflecting element 40 and the stop member 32 may be movable axially relatively to one another, and consequently relative to the clip 20, to cause expansion and/or collapse of the tines 22. For example, the apparatus 10 may include an actuator (not shown) on the proximal end of the apparatus and coupled to the control member 42 and/or the stop member 32 to control their relative movement.

The deflecting element 40 includes one or more ramped surfaces 44 for slidably engaging the tines 22 of the clip 20 and a substantially rounded or otherwise atraumatic distal tip 46 for facilitating advancement of the apparatus 10 through bronchial passages of a patient, as described further below. For example, as shown in FIG. 1A, the distal end 16 of the sheath 12 (shown in phantom) may be advanced against the deflecting element 40 to provide a rounded distal tip of the apparatus 10 to facilitate insertion through bronchial passages. Alternatively, the deflecting element 40 may be shaped to protect the tines 22 and/or prevent them from catching on tissue during advancement through a body lumen such that the sheath 12 may be eliminated.

The control member 42 may extend proximally from the deflecting element 40 through the opening 30 in the clip 20 and/or through the lumen 36 of the stop member 32 such that the deflecting element 40 is located adjacent to and/or distal to the tines 22. Preferably, the opening 30 in the clip 20 and the deflecting element 40 have predetermined mating shapes, allowing the deflecting element 40 to engage the clip 20, e.g., to expand the tines 22, yet be removed proximally through the opening 30 to release the clip 20 from the apparatus 10. Preferably, a proximal portion of the deflecting element 40 has a cross-sectional shape such that, in a first angular orientation, the ramped surfaces 44 may be engaged with the tines 22 to expand them outward without allowing release of the clip 20 from the deflecting element 40. In a second angular orientation, offset from the first orientation by a predetermined angle, the deflecting element 40 may be removed through the opening 30, thereby releasing the clip 20 from the apparatus 10.

Thus, the clip 20 may be releasably coupled to the distal end 16 of the sheath 12 and/or to the deflecting element 40. Alternatively, the clip 20 may be substantially permanently fixed to the distal end 16 of the sheath 12, as described further below.

In addition or alternatively, the apparatus 10 may include a source of electrical energy, e.g., a radio frequency ("RF") generator (not shown), coupled to the proximal end of the sheath 12. The apparatus 10 may include one or more conductors, e.g., insulated wire leads, ribbons, and the like (not shown), that extend along the stop member 32 or the control member 42. For example, wire lead(s) may be embedded within the wall of the stop member 32 or within a lumen that extend between the proximal end and the distal end 34. The wire lead(s) may be coupled to at least a portion of the clip 20 for delivering electrical energy to the clip 20, and consequently to tissue engaged by the tines 22.

In one embodiment, a bipolar arrangement may be used to deliver RF energy to tissue. Two of the tines 22 of the clip 20 may be electrically isolated from one another and coupled to respective lead wires (not shown) that are, in turn, coupled to opposite terminals of the RF generator. For example, the tines 22 may be connected to internal lead wires within the stop member 32 or control member 42 by conductive regions (not shown) on the outer surface of the stop member 32 or control member 42, or by relatively thin lead wires (not shown) designed to break away when the clip 20 is deployed. RF energy may then be able to travel between the tines 22 via tissue engaged by the tines 22, as is well known in the art.

Alternatively, a portion of the clip 20 may be coupled to a first terminal of an RF generator (not shown) and another portion of the apparatus 10, e.g., the distal end 34 of the stop member 32, or the distal end 46 of the deflecting element 40, may be coupled to a second terminal of the RF generator. In a further alternative, a monopolar arrangement may be used, wherein the clip 20 or a portion of the clip 20 is coupled to a first terminal of an RF generator (not shown). An electrode, e.g., an electrode pad (not shown), may be provided that is attachable to an exterior surface of a patient and is coupled to a second terminal of the RF generator. RF energy may then travel between the clip 20 and the external electrode via intervening tissue, particularly tissue engaged by the tines 22, as is also well known in the art.

In a further alternative, the apparatus 10 may include a bronchoscope, endoscope, or other imaging device (not shown), e.g., associated with the sheath 12 for viewing beyond the distal end 16 of the sheath 12, as described above. For example, the bronchoscope may be a separate elongate device and the sheath 12 may include a lumen (not shown) extending between the proximal end and the distal end 16. The bronchoscope may be inserted through the lumen until its viewing lens is disposed adjacent or beyond the distal end 16 of the sheath 12.

Alternatively, the sheath 12 may include a bronchoscope formed into the body of the sheath 12 with a viewing lens, camera, and/or light disposed on or adjacent the distal end 16. For example, the deflecting element 40 may include an imaging device (not shown) in its distal end 46, and one or more optical fibers and/or electrical leads (also not shown) may extend through the control member 42 to the proximal end of the apparatus 10. An external device, e.g., including a processor and/or display (not shown) may be coupled to the proximal end of the bronchoscope and/or apparatus 10, for processing and/or displaying images acquired by the bronchoscope, as is well known in the art.

In yet a further alternative, the sheath 12, stop member 32, or deflecting element 40 may include a fluid lumen (not shown) extending between the proximal and distal ends of the apparatus 10. A source of fluid, e.g., oxygen, air, or saline (not shown), may be connected to the proximal end of the apparatus 10 for introducing fluid into a location beyond the distal end of the apparatus 10 via the fluid lumen. Alternatively or in addition, a source of chemical may be connected to the fluid lumen for injecting corrosive chemicals, bonding agents, conductive fluid, e.g., saline, and the like into a location beyond the distal end of the apparatus 10. In a further alternative, a source of vacuum may be connected to the lumen for evacuating fluid, e.g., air from a location distal to the distal end.

Figure 3A:
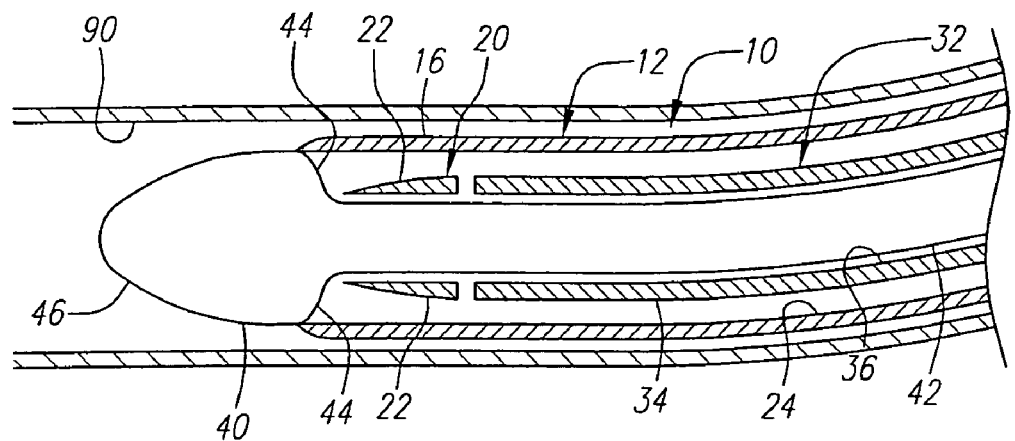
FIGS. 3A–3D are cross-sectional views of a lung, showing a method for isolating a region of the lung.

Turning to FIGS. 3A–3D, the apparatus 10 may be used to deliver a clip 20 into a body lumen, such as a bronchus or other bronchial passage 90, e.g., to substantially isolate a region of a lung and/or to reduce the volume of the lung. The clip 20 may be mounted on or otherwise carried by a distal end 16 of the apparatus 10 with the tines 22 in a contracted condition, e.g., within the lumen 24 of the sheath 12. The distal end 16 may be introduced through a patient's trachea (not shown) using conventional methods, and advanced into the bronchial passage 90, as best seen in FIG. 3A. The passage 90 may communicate with a target region of the lung that is to be isolated, e.g., an upper lobe of the lung or other diseased region (not shown).

Figure 3B:
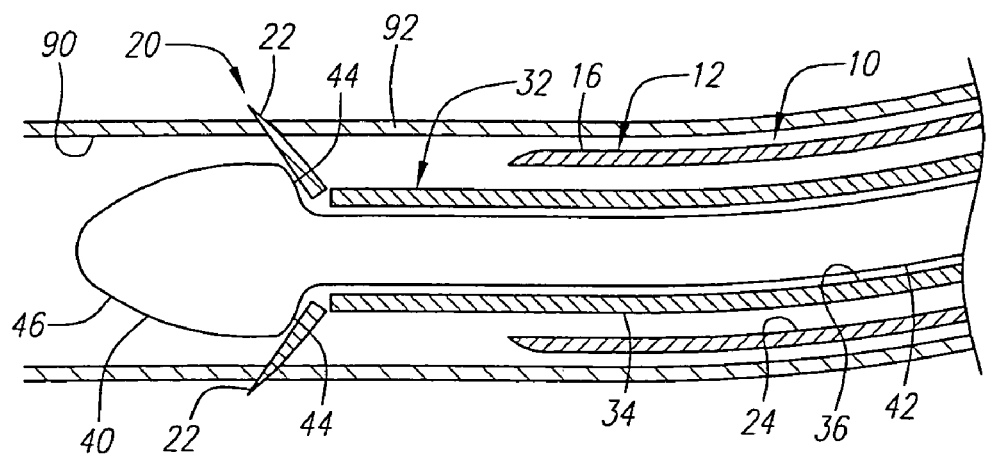

Once the distal end 16 is located at a predetermined location within the passage 90, e.g., a location distal to a branch communicating with the target region of the lung (not shown), the tines 22 may be expanded outwardly towards the expanded condition to engage tissue 92 surrounding the predetermined location, as shown in FIG. 3B. If the apparatus 10 includes a constraint, such as sheath 12, the constraint may be removed, e.g., by retracting the sheath 12 until the clip 20 is exposed from within the distal portion 26 of the lumen 24. The deflecting element 40 may then be moved proximally relative to the clip 20 to drive the tines 22 up along the ramped surfaces 44 and outward into the surrounding tissue 92. The stop member 32 may restrain the clip 20 from moving substantially as the anvil 40 is directed proximally. Alternatively, the stop member 32 may be advanced distally, thereby pushing the clip 20 distally until the tines 22 engage the ramped surfaces 44 and become deflected radially outward to pierce into the surrounding tissue 92. If desired, to enhance penetration of the tines 22 into the surrounding tissue 92, the entire apparatus 10 and/or the deflecting element 40 and stop member 32 may be moved axially, e.g., advanced distally, to drive the tines 22 further into the tissue 92.

Figure 3C:
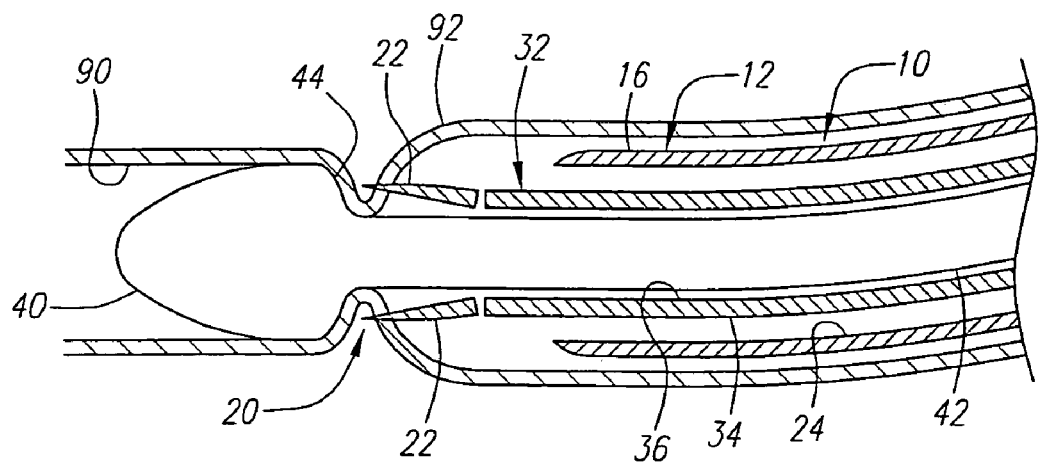

Once the tissue 92 is sufficiently engaged, the tines 22 may be collapsed towards the contracted condition, thereby drawing the surrounding tissue 92 inwardly to substantially close the bronchial passage 90 from air flow through the predetermined location, as shown in FIG. 3C. For example, the deflecting element 40 may be moved distally away from the clip 20, such that the tines 22 are no longer being deflected by the ramped surfaces 44. Because of the resiliency of the tines 22, they may automatically return towards the contracted condition, thereby pulling the tissue 92 inwards. Alternatively, if the tines 22 are plastically deformable, a hammer or other driver (not shown) may be advanced over the clip 20 to force the tines 22 towards the contracted condition, e.g., using the deflecting element 40 as an anvil against which to deform the clip 20.

Figure 3D:
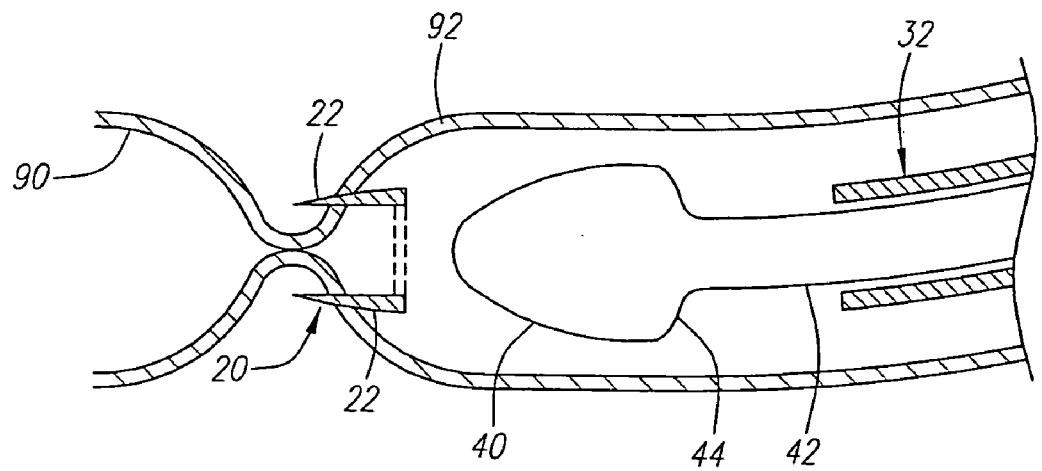

The clip 20 may then be released from the distal end of the apparatus 10 and the apparatus 10 withdrawn from the passage 90, thereby leaving the clip 20 in place, as shown in FIG. 3D. To release the clip 20 from the deflecting element 40, the deflecting element 40 may be rotated relative to the clip 20 until it matches the cross-section of the opening (not shown) through the clip 20, thereby allowing the deflecting element 40 to pass freely through the opening in the clip 20.

In a preferred embodiment, before withdrawing the apparatus 10, energy may be applied to the surrounding tissue 92 after the tines 22 are collapsed towards the contracted condition, e.g., at the stage shown in FIG. 3C. This may cause the surrounding tissue 9 to fuse, scar, or otherwise bond together or otherwise lose its resiliency to return to an open shape. Preferably, the clip 20 is coupled to a source of electrical energy, such as an RF generator (not shown), as described above, for applying electrical energy via the clip 20 to the surrounding tissue 92. Alternatively, other forms of energy may be applied, such as laser energy, ultrasonic energy, and the like. In addition or alternatively, an adhesive or other bonding agent may be introduced into the predetermined location to further enhance the tissue 94 remaining together to substantially close and seal the passage 90.

In an alternative embodiment, the clip 20 may be substantially permanently attached to the apparatus 10, but may be expandable and collapsible, as described above. After using energy and/or a bonding agent to fuse or bond the tissue 92 together, thereby closing the passage 90, the tines 22 may withdrawn from the tissue 92 by withdrawing the entire apparatus 10 from the passage 90.

In a further alternative, the region being isolated may be treated, for example, by introducing an agent into the region before closing the passage 90 with the clip 20. For example, an insufflation lumen (not shown) may be provided in the apparatus 10 that may be used to inflate the region before collapsing and/or releasing the clip 20. Alternatively, a separate insufflation catheter or other device (not shown) may be advanced distally beyond the clip 20 and an agent delivered to the region being isolated immediately before the clip 20 is collapsed.

For example, the region, e.g., a lobe of a lung, may be hyper-inflated with pure oxygen or a low molecular weight gas, such as helium. Once the clip 20 is delivered and the passage 90 substantially closed, the oxygen or helium may slowly be absorbed by the tissue in the isolated region. As this occurs, the region may automatically at least partially collapse, thereby reducing the volume that the region occupies within the patient's chest cavity. Alternatively, a corrosive agent, e.g., for scarring the tissue lining the region being isolated, or a bonding agent, e.g., for promoting the lining to adhere to itself as the region collapses, may be introduced using the insufflation lumen or insufflation catheter. For example, talc is a known agent that may be introduced into the region being isolated in order to cause the walls of the region to scar and/or adhere to one another. Other exemplary materials that may be used are disclosed in PCT Publication No. WO 01/13908, published Mar. 1, 2001, the disclosure of which is expressly incorporated herein by reference.

Alternatively, an electrically conductive fluid, e.g., saline, may be introduced into the region being isolated via the insufflation lumen before releasing or collapsing the clip 20. Once the region is substantially filled with the conductive fluid, electrically energy, e.g., RF energy, may be delivered via the conductive fluid to scar or otherwise damage the tissue. For example, an electrode may be provided on a distal end of the apparatus 10 or an electrode may be electrically coupled via conductive fluid delivered through the insufflation lumen. The conductive fluid may then be removed, e.g., by aspirating via the insufflation lumen.

In a further alternative, a source of vacuum may be used to aspirate any air or other fluid in the region to substantially collapse the region before the passage is closed, either alone or in conjunction with a substance delivered into the region. It will be appreciated that more than one of these insufflation and/or aspiration steps may be performed in a single procedure.

Turning to FIGS. 4–5, another embodiment of a closure device or clip 120 is shown that may be used to isolate a region of a lung, in accordance with the present invention. Generally, the closure device 120 includes an annular body or collar 128 from which a plurality of tines 122 extend. The collar 128 defines an opening 130 therethrough that may allow the closure device 20 to be slidably received over the apparatus 110, as shown in FIG. 6. The tines 122 are movable between a contracted condition (shown in FIGS. 4A and 4B) and an expanded condition (shown in FIGS. 5A and 5B). Although the exemplary embodiment of the closure device 20 shown includes two tines 122, any number of tines may be provided, as will be appreciated by those skilled in the art.

Preferably, the collar 128 is collapsible towards the contracted condition, but is deflectable outwardly towards the expanded condition. In addition, the tines 122 may be deflectable radially outward (see FIG. 7B), but are directable towards one another, e.g., towards an axial orientation, as shown in FIGS. 4A and 4B. The closure device 120 may be formed from a single sheet of biocompatible material, e.g., a metal, such as stainless steel or Nitinol, or plastic.

Figure 7A:
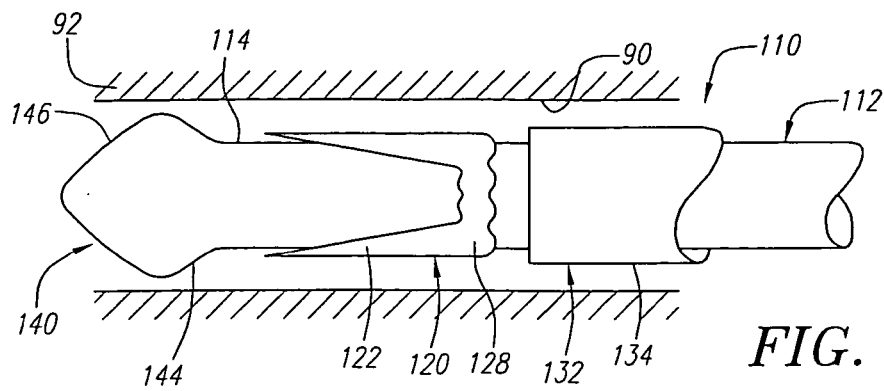
FIGS. 7A–7D are cross-sectional views of a bronchial passage, showing a method for closing the passage using the apparatus of FIG. 6.
Figure 7B:
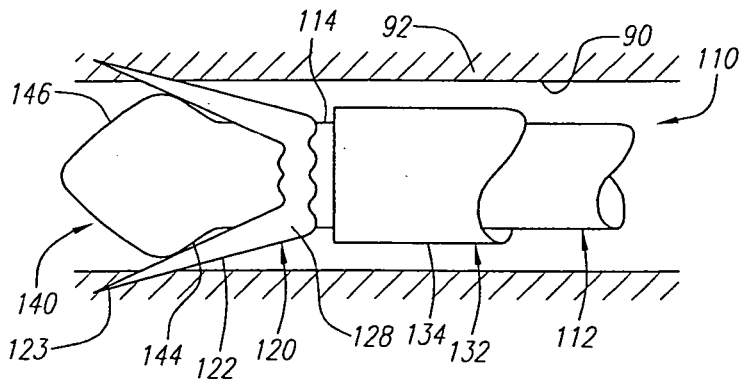

Preferably, the closure device 120 is formed from an elastic or superelastic material, e.g., Nitinol, such that the collar 128 is biased to collapse towards the contracted condition, but may be resiliently expanded to the expanded condition. In addition, the tines 122 may also be biased towards an axial orientation, as shown in FIGS. 4A and 5A, but may be resiliently deflectable radially outwardly (as shown in FIG. 7B).

Figure 7C:
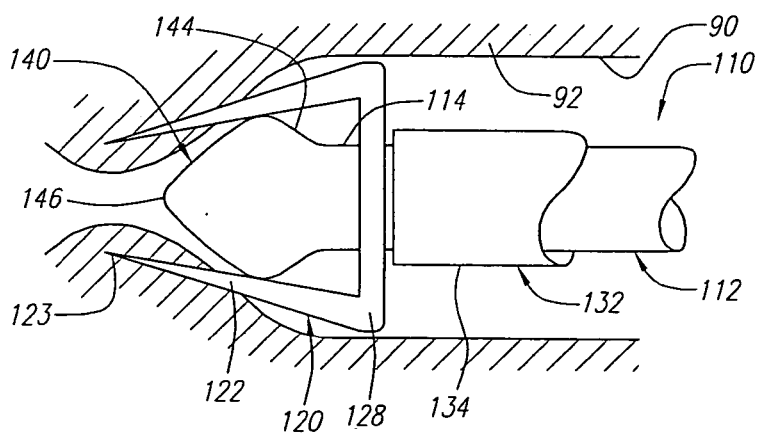
Figure 7D:
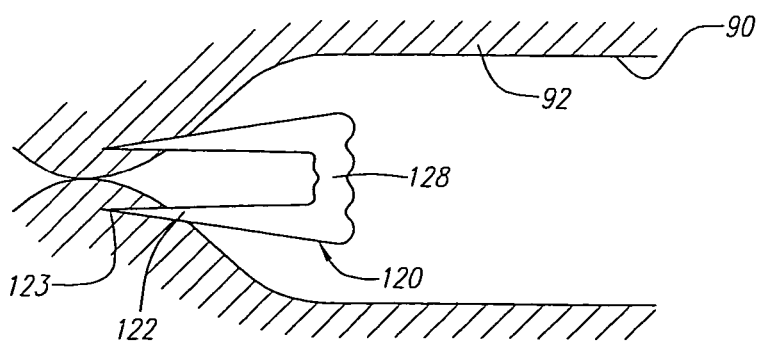

Alternatively, tips 123 of the tines 122 may be biased inwardly towards one another, as shown in FIGS. 7C and 7D. In this alternative, the tines 122 may be deflected axially, as shown in FIG. 7A, to provide a delivery configuration, may be deflected radially outwardly to define an expanded condition, as shown in FIG. 7B, and then may be collapsed towards one another, as shown in FIGS. 7C and 7D. In a further alternative, the collar 128 may be plastically deformable towards the contracted and/or expanded conditions.

Turning to FIG. 6, an apparatus 110 is shown for delivering the closure device 120 that includes an elongate carrier member 112, a pusher member 132, and, optionally a sheath 150 (shown in phantom). The carrier member 112 is an elongate member including a proximal end (not shown), a distal end 114 having a size for insertion into a bronchial passage or other body lumen (not shown), and defining a longitudinal axis 118. Optionally, the carrier member 122 may include one or more lumens (not shown), e.g., for facilitating advancing the apparatus 110 over a guide wire, for delivering a fluid or agent beyond the distal end 114, for aspirating fluid from beyond the distal end 114, and/or for receiving a bronchoscope therethrough, similar to the embodiment described above.

A deflecting element 140 is formed on, attached to, or otherwise carried by the distal end 116 of the carrier member 112. The deflecting element 140 includes one or more ramped surfaces 144 for slidably engaging the tines 122 of the closure device 120. The deflecting element 140 may also include a substantially rounded or otherwise atraumatic distal tip 146 for facilitating advancement of the apparatus 110 through bronchial passages of a patient.

The closure device 120 is disposed on an outer surface 148 of the carrier member adjacent to the deflecting element 140. Preferably, the tips 123 of the tines 122 of the closure device 120 are disposed towards the ramped surfaces 144 and the collar 128 is disposed away from the ramped surfaces 144. The outer surface 148 of the carrier member 112 may be substantially smooth and/or may be coated with a coating. e.g., Teflon, to facilitate sliding the closure device 120 axially along the carrier member 112, particularly if the tines 122 are biased towards one another.

The pusher member 132 is slidably disposed on the carrier member 112 and includes a proximal end (not shown), a distal end 134, and a lumen 136 extending therebetween. The stop member 132 is preferably tubular and may be formed to slidably fit in close proximity to the outer surface 148 of the carrier member 112, i.e., such that the carrier member 112 is slidably disposed within the lumen 136. Preferably, the distal end 134 is substantially blunt and/or of sufficient thickness for abutting and/or otherwise advancing the closure device 120 relative to the carrier member 112, as described further below.

The sheath 150, if included, is an elongate tubular member including a proximal end (not shown), a distal end 152 having a size for insertion into a bronchial passage or other body lumen (not shown), and a lumen 154 extending between the proximal end and the distal end 152. The sheath 150 may be a bronchoscope (not shown) or the sheath 150 may include an additional lumen (not shown) through which a bronchoscope or other device may be advanced, similar to the previous embodiment. Preferably, the distal end 152 of the sheath 150 may be advanced against the deflecting element 140 to provide a rounded distal tip of the apparatus 110, e.g., to facilitate insertion through bronchial passages. Alternatively, the tines 122 may be in sufficient close proximity to the outer surface 148 of the carrier member 112 to prevent them from catching on tissue during advancement through a body lumen such that the sheath 150 may be eliminated.

Optionally, the apparatus 110 may include a source of electrical energy, e.g., an RF generator (not shown), coupled, for example, to the proximal end of the carrier member 112 and/or the pusher member 132. The apparatus 110 may include one or more conductive paths, e.g., extending along the carrier member 112 and/or the pusher member 132 that may coupled to at least a portion of the closure device 120 for delivering electrical energy to the closure device 120, and consequently to tissue engaged by the tines 122, similar to the embodiment described above.

Turning to FIGS. 7A–7D, the apparatus 110 may be used to deliver the closure device 120 into a body lumen, such as a bronchus, bronchiole, or other bronchial passage 90, e.g., to substantially isolate a region of a lung and/or to reduce the volume of the lung. The closure device 120 may be mounted on or otherwise carried by a distal end 114 of the carrier member 112 preferably with the tines 122 and collar 128 biased towards the contracted condition, as described above.

The distal end 114 of the carrier member 112 may be introduced through a patient's trachea (not shown) using conventional methods, and advanced into the bronchial passage 90, as best seen in FIG. 7A. The passage 90 may communicate with a target region of the lung that is to be isolated, e.g., an upper lobe of the lung or other region that includes substantially diseased and/or damaged tissue (not shown). The carrier member 112 may be covered by a sheath (not shown), or may be inserted through a lumen of a bronchoscope (also not shown), as described above.

Once the distal end 114 is located at a predetermined location within the passage 90, e.g., a location distal to a branch communicating with the target region of the lung (not shown), the sheath may be retracted (if provided), and the pusher member 132 may be advanced distally relative to the carrier member 112. As the pusher member 132 is advanced, the distal end 134 of the pusher member 132 may engage the collar 128 of the closure device 120, thereby advancing the clip 122 distally along the carrier member 12. As the tips 123 of the tines 122 slidably engage the ramped surfaces 144, the tines 122 are directed radially outwardly until they are driven into tissue 92 surrounding the passage 90, as best seen in FIG. 7B.

Turning to FIG. 7C, the pusher member 132 may be advanced further until the collar 128 of the closure device 120 engages the ramped surfaces 144 of the deflecting element 140. This causes the collar 128 to expand outwardly towards the expanded condition. In the expanded condition, the opening 130 (see FIG. 5B) may allow the closure device 120 to be advanced over the deflecting element 140. As the closure device 120 is advanced over the deflecting element 140, the tines 122, because of their natural bias, begin to return towards the contracted condition, thereby drawing the surrounding tissue 92 inwards to substantially close the passage 90, as shown in FIG. 7C.

If desired, electrical energy may then be applied to scar, expand, and/or otherwise fuse the surrounding tissue 92 to enhance closure of the passage 90. In addition or alternatively, oxygen or other fluid may be insufflated into the region beyond the closure device 120 and/or fluid may be aspirated from the region beyond the closure device 120. Furthermore, agents, e.g., corrosive or bonding agents, or electrically conductive fluid, may be introduced into the region, all similar to the previous embodiment.

As shown in FIG. 7D, once the tines 122 are substantially engaged with the surrounding tissue 92 and/or begin to collapse towards the contracted condition, the apparatus 110 may be withdrawn from the passage 90, leaving the closure device 120 implanted within the passage 90. As the apparatus 110 is withdrawn, resilient expansion of the collar 128 may allow the deflecting element 140 to be withdrawn through the opening 130 in the collar 128. Alternatively or in addition, the bias of the tines 122 towards the contracted condition may cause the collar 128 to at least partially expand towards the expanded condition until the deflecting element 140 is removed. Once the closure device 120 passes distally beyond the deflecting element 140, the collar 128 may collapse substantially towards the contracted condition and/or the tines 122 may contract inwardly, as shown in FIG. 7D.

In an alternative embodiment, tines (not shown) similar to those on the closure device 120 may be substantially permanently attached to the apparatus 110, that may be expandable and collapsible, similar to the tines 122 described above. After using energy and/or a bonding agent to fuse or bond the tissue 92 together, thereby closing the passage 90, the tines may withdrawn from the tissue 92, e.g., by withdrawing the entire apparatus 10 from the passage 90, similar to the previous embodiment.

Figure 8A:
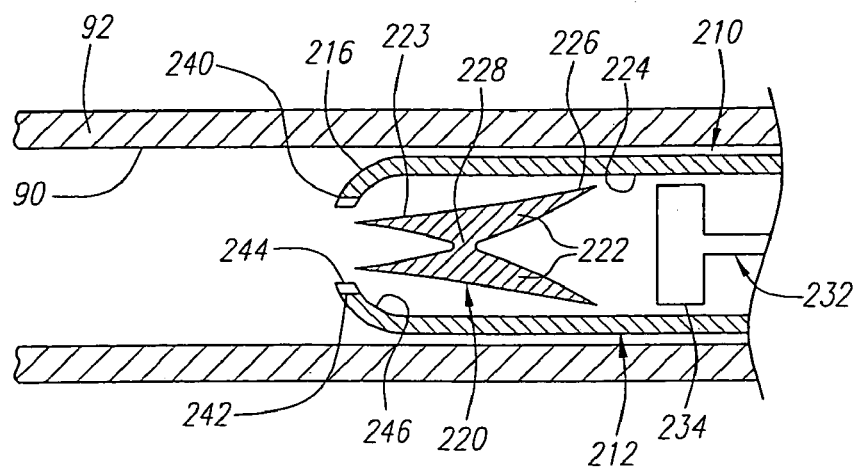
FIGS. 8A–8C are cross-sectional views of a bronchial passage, showing another apparatus and method for closing a passage.
Figure 8B:
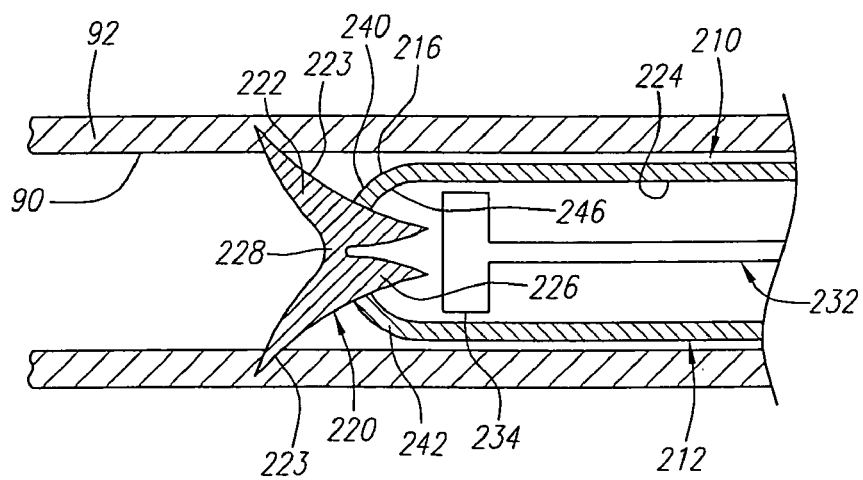
Figure 8C:
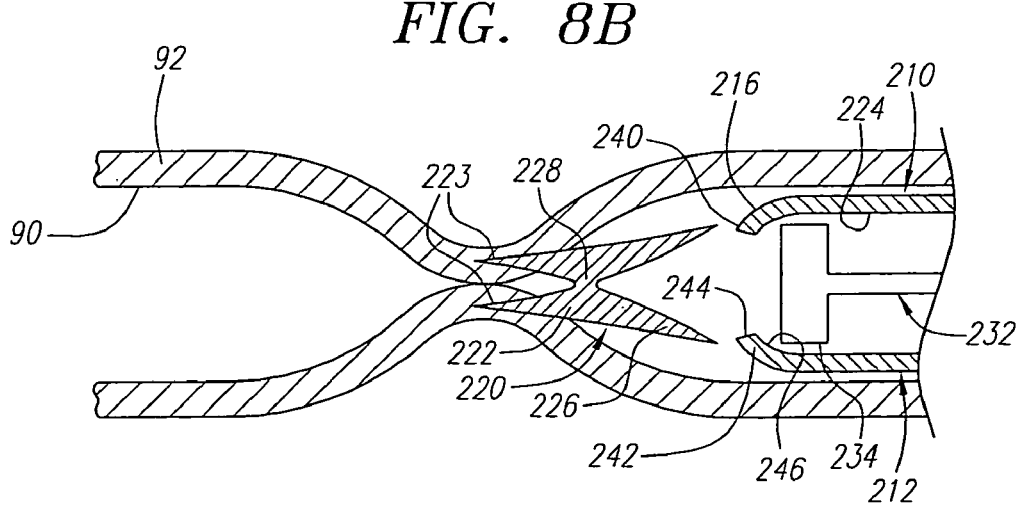

Turning to FIGS. 8A–8C, yet another apparatus 210 is shown for closing a passage 90, such as a bronchial passage communicating with a region of a lung to be isolated. Generally, the apparatus 210 includes a sheath 212, a closure device or clip 220 carried by the sheath 212, and a pusher member 232 for deploying the closure device 220. The sheath 212 is an elongate tubular member including a proximal end (not shown), a distal end 216 having a size for insertion into a bronchial passage or other body lumen (not shown), and a lumen 224 therebetween defining a longitudinal axis 218.

A deflecting element 240 is formed on or attached to the distal end 216 of the sheath 212. Preferably, the deflecting element 240 includes one or more shoulders 242 defining a narrow outlet 244 communicating with the lumen 224. The shoulders 242 include proximal surfaces 246 that may be ramped or may be substantially blunt.

The closure device 220 includes a plurality of elongate elements or tines 222, each of which includes a first end 223 defining a tissue penetrating tip, and a second end 226 opposite the first end 223. A hinged region 228 pivotally couples the elongate elements 222 together, e.g., at intermediate regions, such that the first ends 223 are movable from a contracted condition away from one another towards an expanded condition, preferably when the second ends 226 are directed towards one another.

Preferably, the elongate elements 222 are substantially rigid such that they pivot about the hinged region 228. For example, when the second ends 226 are directed radially inwardly, the first ends 223 are directed radially outwardly, and vice versa. The elongate elements 222 may also be substantially straight or slightly curved such that the elongate elements define outer surfaces that may be slidably engaged with the deflecting element 240, as described further below.

In a preferred embodiment, the closure device 220 is formed from an elastic or superelastic material, e.g., Nitinol, such that the first ends 223 are biased towards one another, as shown in FIG. 8A, thereby defining the contracted condition. The closure device 220 may be resiliently deflected such that the first ends 223 are directed radially outwardly away from one another, as shown in FIG. 8B, thereby defining the expanded condition. Preferably, the first ends 223 are directed towards each other in the contracted condition such that a cross-section of the closure device 220 at the first ends 223 is substantially smaller than at the second ends 226. More preferably, a cross-section of the closure device 220 at the intermediate regions is also substantially smaller than at the second ends 226 in the contracted condition.

The pusher member 232 includes a distal end 234 that is disposed within the lumen 224 proximal to the closure device 220. Preferably, the distal end 234 slidably engages an inner wall of the sheath 212 defining the lumen 224, thereby ensuring that the distal end 234 substantially abuts the second ends 226 of the closure device 220, which may be blunt or pointed. The pusher member 232 is slidable relative to the sheath 212 for engaging the second ends 226 of the closure device 220 with the distal end 234 of the pusher member 232, e.g., for ejecting the closure device 220 from the lumen 224, as described below.

In addition, similar to the embodiments described above, the apparatus 210 may include a bronchoscope, an RF generator, lumens and sources of fluid or agents (not shown), as will be appreciated by those skilled in the art.

Use of the apparatus 110 proceeds similarly to the embodiments described above. As shown in FIG. 8A, the apparatus 110 may be introduced into a lung or other body lumen until the distal end 216 is disposed at a predetermined location, e.g., within a bronchial passage 90 communicating with a region of the lung to be isolated (not shown). Once the predetermined location has been reached, the pusher member 232 may be advanced distally relative to the sheath 212.

Preferably, as shown, the cross-section of the closure device 220 at the first ends 223 is substantially smaller than the distal outlet 244. Thus, as the pusher member 232 is advanced, the first ends 223 pass through the distal outlet 244 into the passage 90. As the closure device 220 partially exits the lumen 224, the shoulders 242 slidably engage the outer surfaces of the elongate elements 222 of the closure device 220, e.g., proximate the intermediate regions. As the closure device 220 is deployed further, the shoulders 242 apply a radially compressive force, causing the second ends 226 of the closure device 220 to move radially inwardly. Because the elongate elements 222 pivot about the hinged region 228, this causes the first ends 223 to extend radially outwardly and into the surrounding tissue 92, as shown in FIG. 8B.

As the pusher member 232 advances to push the remainder of the closure device 220 through the distal outlet 244, the second ends 226 clear the shoulders 242, thereby removing the radially compressive force being applied to the second ends 226. Because of the bias of the hinged region 228, the second ends 226 expand outward, and the first ends 223 collapse inwardly, thereby drawing the surrounding tissue 92 inwardly, as shown in FIG. 8C.

The apparatus 210 may then be withdrawn, leaving the closure device 220 in place to hold the passage 90 closed. In addition, electrical energy, bonding agents, and the like may be used in conjunction with the closure device 220 to substantially close the passage 90, similar to the embodiments described above.

Figure 9A:
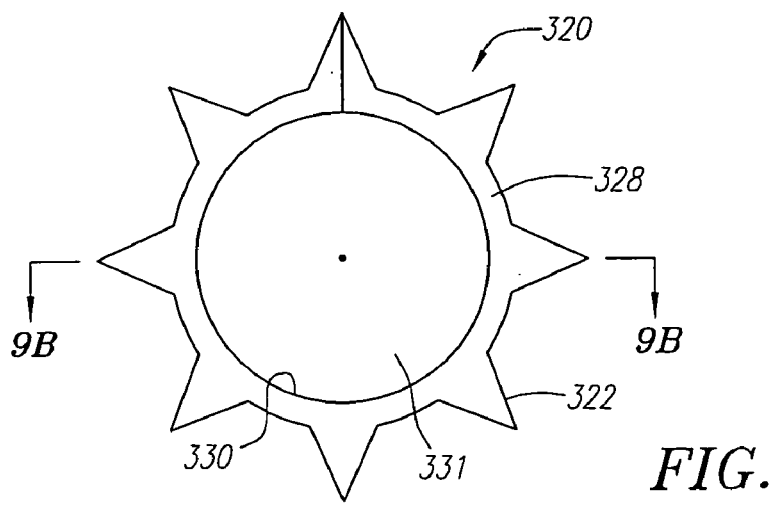
FIGS. 9A and 9B are front and cross-sectional side views, respectively, of yet another embodiment of a closure device in an expanded condition, in accordance with the present invention.
Figure 9B:
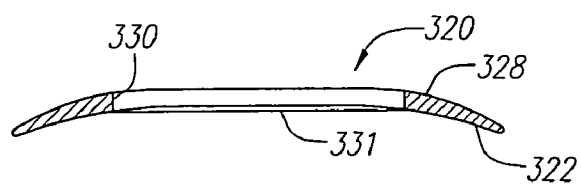

Turning to FIGS. 9A–9D, yet another embodiment of a closure device or clip 320 is shown for closing a bronchial passage or other body lumen (not shown). The closure device 320 generally includes an annular body 328 defining a central region 330 from which a plurality of tines 322 extend. The closure device 320 is movable between an expanded condition and a contracted condition. In the expanded condition, the tines 322 preferably extend radially outwardly away from the annular body 328 such that the closure device 320 defines a generally planar configuration, as shown in FIGS. 9A and 9B.

Figure 10A:
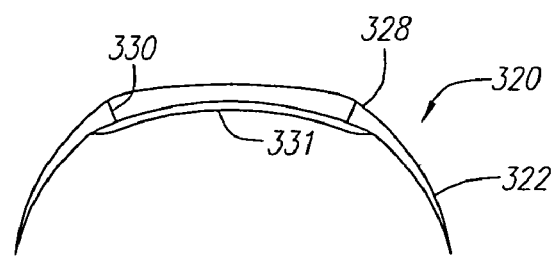
FIGS. 10A and 10B are cross-sectional side and side views, respectively, of the closure device of FIGS. 9A and 9B in a contracted condition.
Figure 10B:
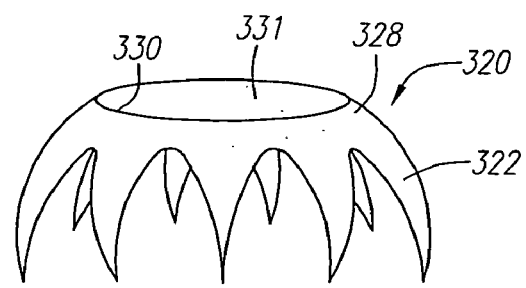

In the contracted condition, the tines 322 may be deflected towards one another, such that the closure device 320 defines a generally concave configuration, as shown in FIGS. 10A and 10B. Alternatively, the annular body 328 may be compressed inwardly, similar to the closure device shown in FIG. 4B. Preferably, the closure device 320 is formed from an elastic or superelastic material, e.g., Nitinol, such that the closure device 320 is biased towards the expanded condition, but may be compressed towards the contracted condition to facilitate delivery, as described further below.

A flexible membrane 331 is secured across the central region 330 of the closure device 320, thereby substantially sealing the central region 330 from fluid flow therethrough. The flexible membrane 331 may be formed from a variety of biocompatible materials, such as [preferred materials?]. The membrane 331 may be elastic, e.g., stretched across the central region 330, to accommodate compression and expansion of the closure device 320. Alternatively, the membrane 331 may be substantially inelastic, e.g., attached to the annular body 328 in the expanded condition such that the membrane 331 extends across the central region 330. The membrane 331 may be folded, crumpled, or otherwise furled when the closure device 320 is compressed towards the contracted condition. The membrane 331 may increase the flexibility of the closure device 320 to move between its contracted an expanded conditions. In a further alternative, the closure device 320 may be formed from sufficiently flexible material that the central region 330 may be eliminated, i.e., the closure device may include a solid body (not shown) rather than the annular body 328.

Figure 11A:
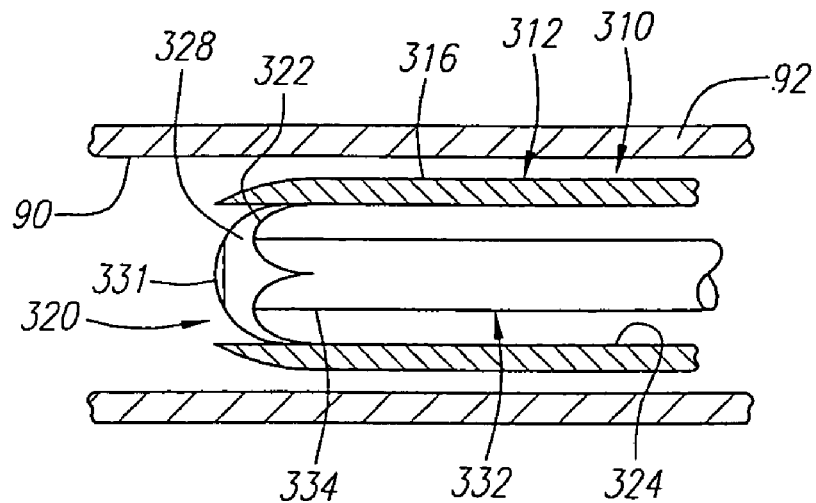
FIGS. 11A and 11B are cross-sectional views of a bronchial passage, showing a method for closing the passage using the closure device of FIGS. 9 and 10.
Figure 11B:
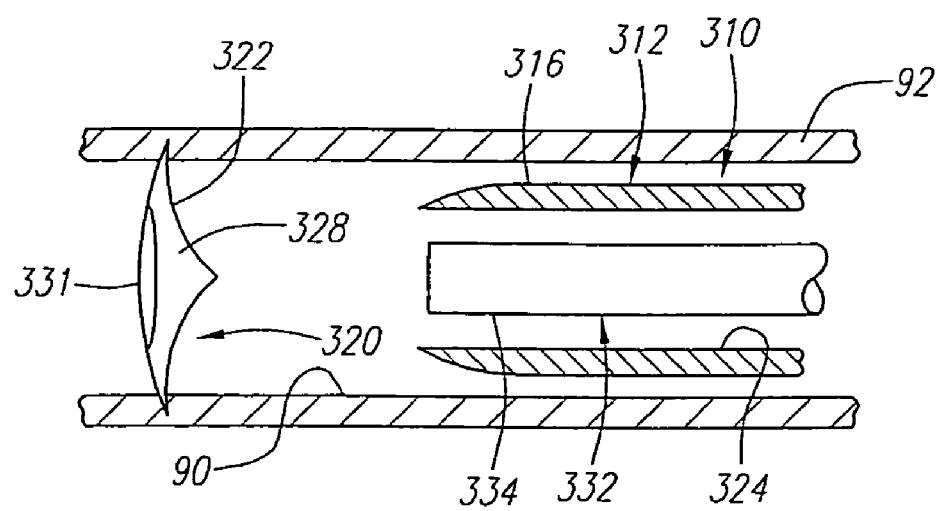

Turning to FIGS. 11A and 11B, the closure device 320 may be delivered and implanted using an apparatus 310, similar to those described above. Generally, the apparatus 310 includes a sheath 312 including a lumen 324 extending between its proximal end (not shown) and its distal end 316. The closure device 320 is disposed within the lumen 324 in the contracted condition. In the contracted condition, the membrane 331 may elastically shrink and/or may be folded, crumpled, or otherwise furled. A pusher member 332 is slidably disposed within the lumen 324 such that a distal end 334 of the pusher member 332 is disposed proximal to the closure device 320. The sheath 312 constrains the closure device 320 in the contracted condition within the lumen 324.

Although the tines 322 are shown being directed proximally towards the pusher member 332, it will be appreciated that the tines 322 may be reversed, i.e. directed away from the pusher member 332. Preferably, the inner wall of the sheath 312 is coated with a material, e.g., Teflon, to facilitate slidably deploying the closure device 320 from the lumen 324.

With particular reference to FIG. 11A, the apparatus 310 is introduced into a patient's trachea and advanced into a bronchial passage until the distal end 316 of the sheath 312 reaches a predetermined location. Preferably, the predetermined location is a bronchus, bronchiole, or other passage 90 that communicates with a diseased region or other region of a lung that is to be isolated.

As shown in FIG. 11B, the pusher member 332 is advanced distally, thereby deploying the closure device 320 from the lumen 324 into the passage 90. Once the tines 322 are released within the passage 90, the closure device 320 preferably expands towards its expanded planar condition, thereby causing the tines 322 to engage and/or penetrate into surrounding tissue 92. The membrane 331 expands, possibly stretching and/or unfurling, as the closure device 320 expands to extend across the passage 90 to substantially seal the passage 90 from air flow therethrough. The apparatus 310 may then be withdrawn, leaving the closure device 320 within the passage 90 to substantially close and/or seal the passage 90. Similar to the embodiments described above, the procedure may be monitored using a bronchoscope and the like. In addition, a fluid, bonding agent, and/or corrosive agent may be introduced beyond the closure device 320 to further enhance isolation and/or collapse of the region of the lung beyond the closure device 320.

Figure 12:
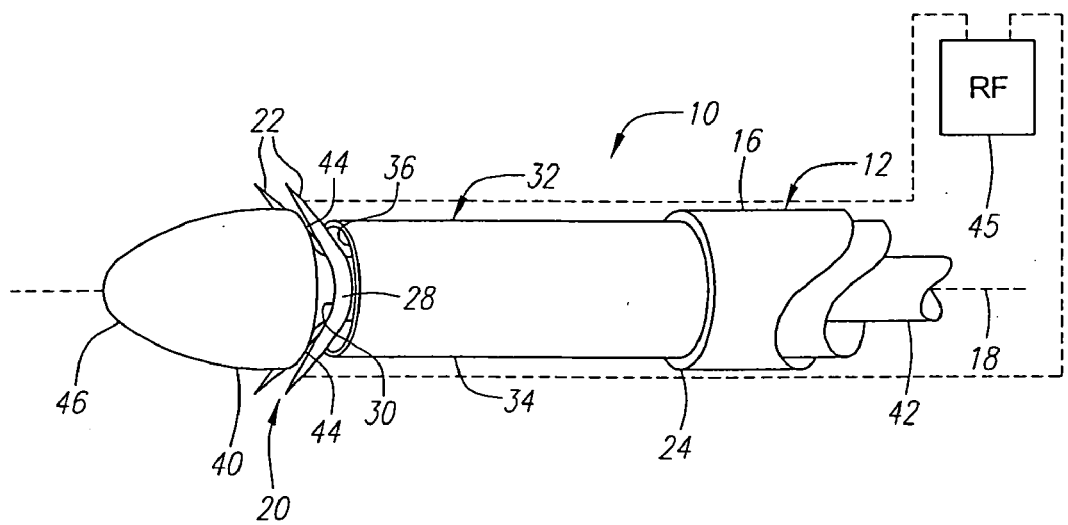
FIG. 12 is a perspective view similar to the cross-sectional view shown in FIG. 3B, and also showing coupling of the closure device to an RF generator.

FIG. 12 illustrates closure means of FIG. 3B in which the tines 22 are coupled to a radio frequency generator.

Figure 13:
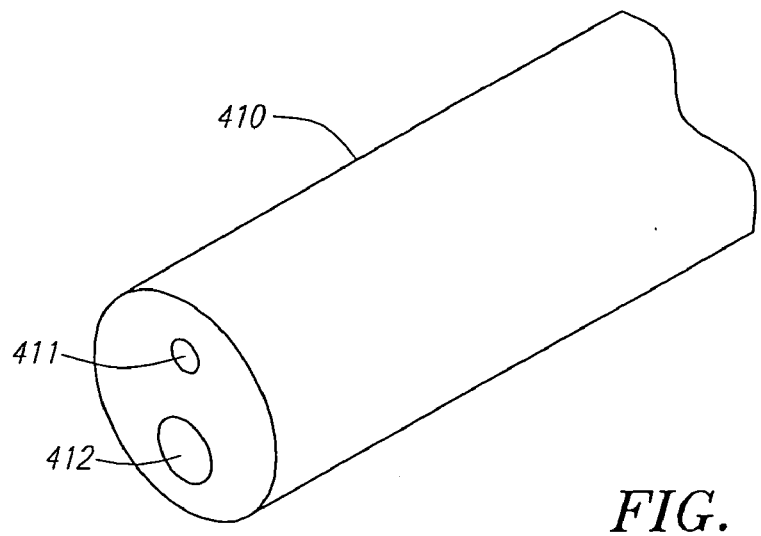
FIG. 13 illustrates a two-lumen device in which a second lumen is provided which may be used for various functions, including infusion and/or aspiration.

FIG. 13 illustrates elongate member 410 having separate limens 411 and 412, one of which may be used to insufflate or aspirate at the distal end of the elongate member.

Thus, a closure device and/or apparatus in accordance with the present invention may be used to substantially isolate a region of a lung and/or to reduce the volume of the lung without need for open surgery. Thus, trauma to the patient may be minimized and/or recovery time may be accelerated as compared to conventional LVRS.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for closing a bronchial passage, comprising:
   an expandable body having a substantially planar configuration in its expanded condition and having an opening therethrough and including a plurality of tines extending from the body away from the opening, the body being compressible from an expanded condition towards a contracted substantially annular condition for facilitating introduction into a bronchial passage; and
   a flexible membrane extending across the opening for substantially sealing the opening from air flow therethrough.

2. The device of claim 1, wherein the tines extend radially outwardly from the body in the expanded condition, thereby defining the substantially planar configuration.

3. The device of claim 2, wherein the tines are deflected towards one another in the contracted condition such that the body defines a concave configuration.

4. The device of claim 2, wherein the tines are biased towards the expanded condition.

5. A method for reducing volume of a lung using an expandable closure device which, in its expanded condition, has a substantially planar configuration from which a plurality of tines extend, the tines being movable between substantially annular contracted and substantially planar expanded conditions, the method comprising:
   advancing the closure device in the contracted condition along a bronchial passage to a predetermined location; and
   expanding the tines outwardly towards the expanded condition to engage tissue surrounding the predetermined location, whereby the planar body substantially seals the bronchial passage from air flow through the predetermined location.

6. The method of claim 5, wherein the planar body has an annular opening across which a flexible membrane extends substantially sealing the opening from airflow therethrough, and wherein the flexible membrane accommodates compression and expansion as the tines are compressed and expanded.

7. The method of claim 5, wherein the tines are constrained in the contracted condition by a delivery apparatus carrying the closure device, and wherein the expanding step comprises deploying the closure device from the delivery apparatus, whereupon the tines automatically expand towards the expanded planar condition.

* * * * *